United States Patent
Radziuk et al.

(10) Patent No.: US 6,229,604 B1
(45) Date of Patent: *May 8, 2001

(54) DETECTOR DEVICE TO BE USED IN ATOMIC ABSORPTION SPECTROSCOPY

(75) Inventors: Bernhard Radziuk, Frickingen; Gunter Rodel, Owingen, both of (DE)

(73) Assignee: Bodenseewerk Perkin-Elmer GmbH (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/139,245

(22) Filed: Aug. 25, 1998

(30) Foreign Application Priority Data

Sep. 12, 1997 (DE) .............................. 197 40 211

(51) Int. Cl.[7] ...................................................... G01J 3/02
(52) U.S. Cl. ............................................ 356/326; 356/328
(58) Field of Search ................................ 356/326, 328, 356/300; 250/208.2

(56) References Cited

U.S. PATENT DOCUMENTS 4,958,928 * 9/1990 Kuderer ........................... 356/328

FOREIGN PATENT DOCUMENTS

WO 91/03714 * 3/1991 (WO) ................................ 356/328

* cited by examiner

Primary Examiner—F. L. Evans
(74) Attorney, Agent, or Firm—St. Onge Steward Johnston & Reens LLC

(57) ABSTRACT

The invention refers to a photoelectric detector device to be used in the atomic absorption spectroscopy. This device is characterized by a photo semiconductor array having a plurality of photo semiconductor devices and a read-out means for jointly reading out the charges generated in the photo semiconductor devices of any continuous portion in the photo semiconductor array by means of impingement of radiation, and for generating electric signals corresponding to the read-out charges.

13 Claims, 5 Drawing Sheets

DETECTOR DEVICE TO BE USED IN ATOMIC ABSORPTION SPECTROSCOPY

TECHNICAL FIELD

The present invention refers to a photoelectric detector device to be used in atomic absorption spectroscopy.

BACKGROUND ART

Photoelectric detector devices of that kind, are known in the field of the atomic absorption spectroscopy, for instance in the form of photo semiconductor devices.

The photo semiconductor devices in a detector device of that kind may exist in the form of photo diodes, CCD structures etc.

However, the signal/noise ratio of known detector devices of that kind depends on the portion of the detector face that is actually loaded by a radiation to be detected. An aggravated signal/noise ratio in particular results if not the entire detector face but only a small part thereof is loaded by the radiation to be detected.

SUMMARY OF THE INVENTION

Thus, the object underlying the invention is to improve the known photoelectric detector device.

This object is achieved by a detector device which is characterized by a photo semiconductor array having a plurality of photo semiconductor devices and a read-out means for jointly reading out the charges generated by impingement of radiation onto the photo semiconductor device of any continuous portion within the photo semiconductor array, and for generating electric signals corresponding to the read-out charges.

By means of a detector device designed in that manner, only the charges generated by impingement of radiation in any continuous portion of the photo semiconductor array can be read out by means of the read-out means. Through this it is possible to only read out charges from that part of the photodetector onto which the radiation to be detected or measured actually impinges. Those portions which in the known detectors make a great contribution to the signal/noise ratio, i.e. those portions that do not deliver a measuring signal but merely lead to a read-out noise are therefore not taken into consideration by the read-out device.

In accordance with an advantageous development, the detector device comprises a plurality of inputs each being assigned to a photo semiconductor device of the photo semiconductor array, an output for the generated electric signals which correspond to the read-out charges, a switching means having at least one switch associated to at least one input, each switch being provided downstream each input associated thereto, and by means of each switch each input associated thereto can be coupled to the output of the read-out device.

By means of this embodiment, which merely comprises simple electronic components, the invention can be realized in an especially reasonable manner.

In accordance with a further embodiment, a switch may be assigned to a plurality of inputs. Since this embodiment requires less components, it is in particular advantageous if the photo semiconductor array is designed symmetrically with respect to an axis, and the face of the detector device shall be enlarged or reduced only symmetrical with respect to this axis.

Each switch of the switching means may preferably be electrically operable. In this case each switch can be controlled quickly and reliably by electric signals supplied to the read-out device.

In an advantageous embodiment a device may additionally be provided to each switch, said device putting all photo semiconductor devices which are not coupled to the output of the read-out device to a predetermined potential. Thus, possible influences of photo semiconductor devices on the circuit, from which charges are not to be read out, are minimized.

For this purpose each device associated to a switch may for instance have a further switch, which is provided between the input associated to the switch and the predetermined potential such that it couples the input—when it is not coupled to the output of the read-out device—to the predetermined potential. Furthermore, the switch and the switch associated thereto may be provided in an operative manner by an electric signal which is supplied to the switch directly and to the associated switch via an inverter.

Moreover, a decoding means can be provided, which in response to digital selection signals operates the switch(es). Thereby it is possible to easily control a plurality of switches electronically, i.e. by means of a processor means.

According to a further advantageous embodiment, a power limiting means, e.g. in the form of a diode, can be provided directly after each input in the read-out device. Such a power limiting means ensures that the read-out device responds not until reaching a predetermined threshold value.

According to an advantageous embodiment, the detector device comprises an amplifier device having an operational amplifier for amplifying the electric signals of the read-out device and a variable capacitance connected in parallel to the amplifier.

Thereby the sensitivity range of the detector can be adjusted in a simple manner by varying the capacitance. By selecting the sensitivity range in response to the signal to be measured, the signal/noise ratio can moreover be optimized.

Such a variable capacitance can in an especially reasonable manner be composed of arrays connected in parallel each consisting of a capacitor and a switch, the capacitance being variable by operating at least one switch.

Furthermore, an additional switch may be provided in parallel to the arrays each consisting of a capacitor and a switch. This measure causes the integrator circuit consisting of the operational amplifier and the variable capacity to be set back in an especially simple and quick manner.

In accordance with a further purposeful embodiment, a decoder means may be used for operating the switches of the variable capacitance, said decoder means operating the switches in response to digital selection signals. Through this an especially simple change of the capacitance in a means having a plurality of parallel connected arrays of capacitors and switches is possible by means of few selection signals.

Further advantages of the invention can be derived from the following exemplary description of preferred embodiments of the invention with reference to the drawings.

DETAILED DESCRIPTION OF THE PREFERRED EMBODIMENTS

Figure 1:
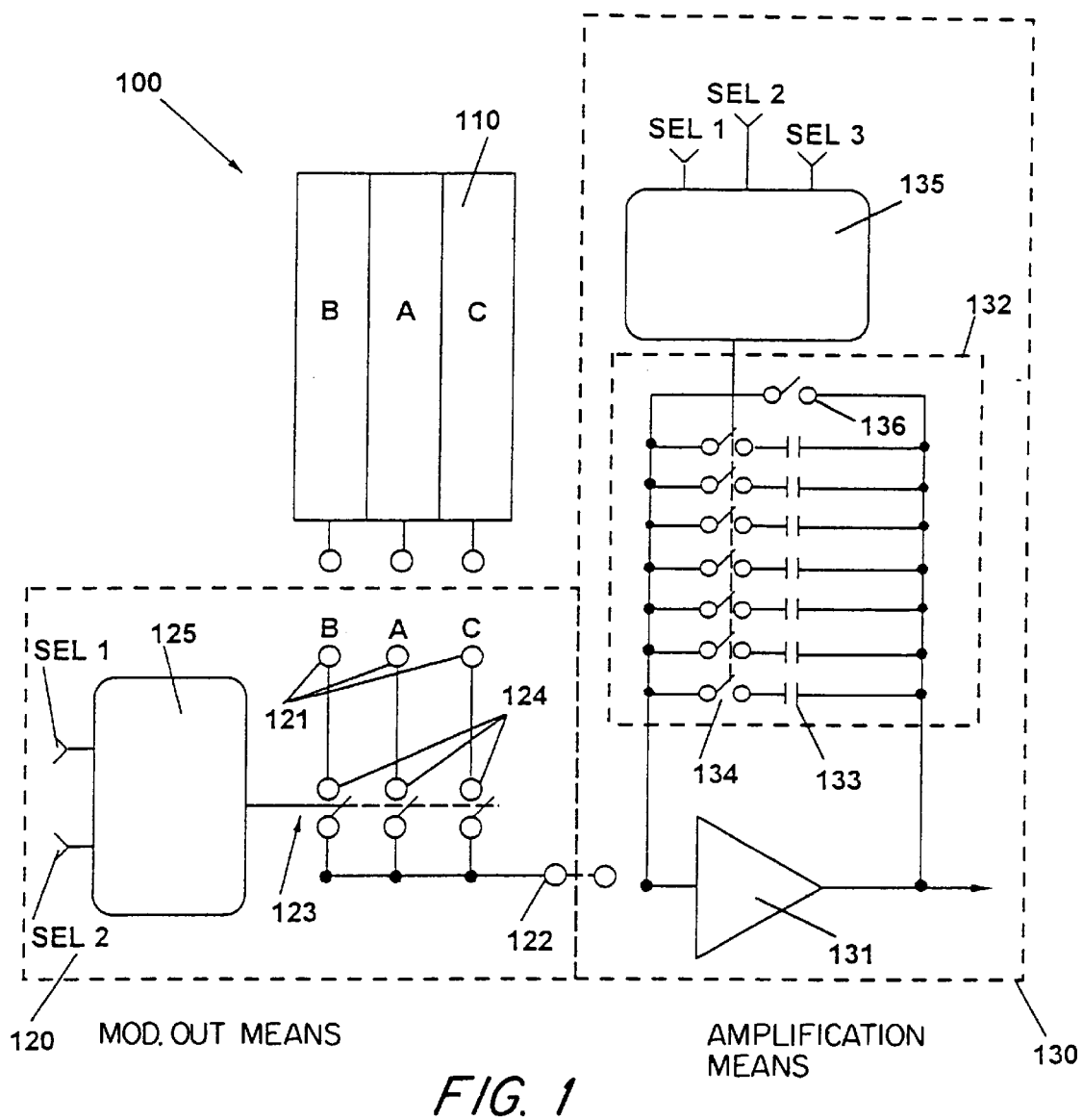
FIG. 1 shows a detector device according to a first embodiment of the invention.

FIG. 1 shows a first embodiment 100 of the detector device.

The detector device 100 comprises a photo semiconductor array 110, a read out means 120 and an amplification means 130.

The photo semiconductor array 110 comprises a plurality of photo semiconductor devices A, B and C for converting light, which impinges onto the photo semiconductor devices, into charges. Photo semiconductor devices that can be used are all known photo semiconductor devices, such as photodiodes, CCD structures and the like. The charges generated in each photo semiconductor device may be read out by means of the read-out means 120 via an output of each photo semiconductor device.

The dimensions of the photo semiconductor devices may be adapted in accordance with the respective measuring arrangement. If, for instance, the gap of a monochromator is to be imaged onto the detector device, it is purposeful to form the height of all photo semiconductor devices A, B and C corresponding to the height of the image of the gap which is to be projected onto the detector device. Since in such a design in height direction, the entire detector is irradiated, an optimum signal/noise ratio results in the height direction. The width of the photo semiconductor devices practically also depends on the expected widths of the image projected onto the detector device.

The read-out means 120 of the detector device 100 is provided with inputs 121. One of the photo semiconductor devices A, B and C, is each associated to each input. The inputs 121 are connected in a suitable manner to the respective photo semiconductor devices A, B and C, respectively. Furthermore, the read-out means 120 comprises and output 122 at which electric signals corresponding to the charges read-out by the read-out means are output.

The read-out means 120 further comprises a switch means 123 having three switches 124. In the read-out means 120 each switch 124 is provided between one of the inputs 121 of the read-out means 120 and the output 122 of the read-out means.

The switches 124 are operative by means of electric signals. In accordance with FIG. 1, a decoder means 125 is provided for operating the switches, said decoder means controlling switches 124 in response to two selection signals SEL1 and SEL2. As an alternative to the decoder means 125, the switches 124 may, however, also be directly controlled by appropriate electric signals.

As can be taken from FIG. 1, any combination of photo semiconductor devices A, B and C can be connected with the output of the read-out means by appropriately closing the switches 124. If such a connection with the output 122 is established, the charges generated in the respective photo semiconductor devices are output in the form of an electric signal to the output 122 of the read-out means 120.

In particular, by appropriately positioning the switches 124 the continuous portions A, B, C, A and B as well as A and C can be read-out through the read-out means, wherein the portions B and C, A and C, A and B, C or B, respectively are not taken into consideration. On the whole the signal/noise ratio of the detector device may be improved if only a part of the detector face is required for detecting a radiation.

The output 122 of the read-out means is connected to the input of an amplification means 130. This amplification means comprises an operational amplifier 131 and a variable capacitance 132 connected in parallel to the operational amplifier.

In accordance with FIG. 1, the variable capacitance is constructed of arrays composed of one capacitor 133 and one switch 134, said arrays being connected in parallel to one another. The capacitance of the variable capacitance may be easily changed by operating the switches 134. For this purpose a further decoder means 135 is provided which controls the switches in response to the selection signals SEL1, SEL2 and SEL3. As an alternative to the decoder means 135, the switches can of course also be controlled directly by appropriately supplied signals.

The operational amplifier 131 and the variable capacitance 132 represent a current integrator in the circuit shown in FIG. 1, which integrates the power signal which is supplied by the read-out circuit 120 to a voltage taken can be tapped at the output of the amplifier means 130. This output voltage is proportional to the charges generated in the photo semiconductor devices which are connected through the switching means with the output 122 of the read-out means.

Furthermore, a circuit 136 is connected in parallel to the arrays composed of one capacitor and one switch each is provided in accordance with FIG. 1. The integrator switch can easily be reset by means of this switch. This switch 136 may also be controlled by the decoder means or as an alternative by an electric signal directly applied.

By changing the capacitance, the sensitivity range of the detector device can be easily selected and thus the most favorable signal/noise ratio can be adjusted for the detector device in accordance with the measuring signal.

The values of the capacitors of the variable capacitance 132 are selected in a purposeful manner in accordance with the measuring range to be expected. In order to enable for instance a possibly universal use of the detector in various atomic absorption methods, seven capacitors having values 0.1 pF, 0.4 pF, 1 pF, 2.5 pF, 7 pF, 12 pF and 20 pF may be selected in the variable capacitance 132. By this selection, capacitances in the range of 0.1 to 32 pF can be connected. If the inherent dynamics of a semiconductor detector with 3000 is taken into consideration, a dynamic range of approximately $1 \times 10^6$ results for the present circuit composed of photo semiconductor array and amplifier.

Figure 2:
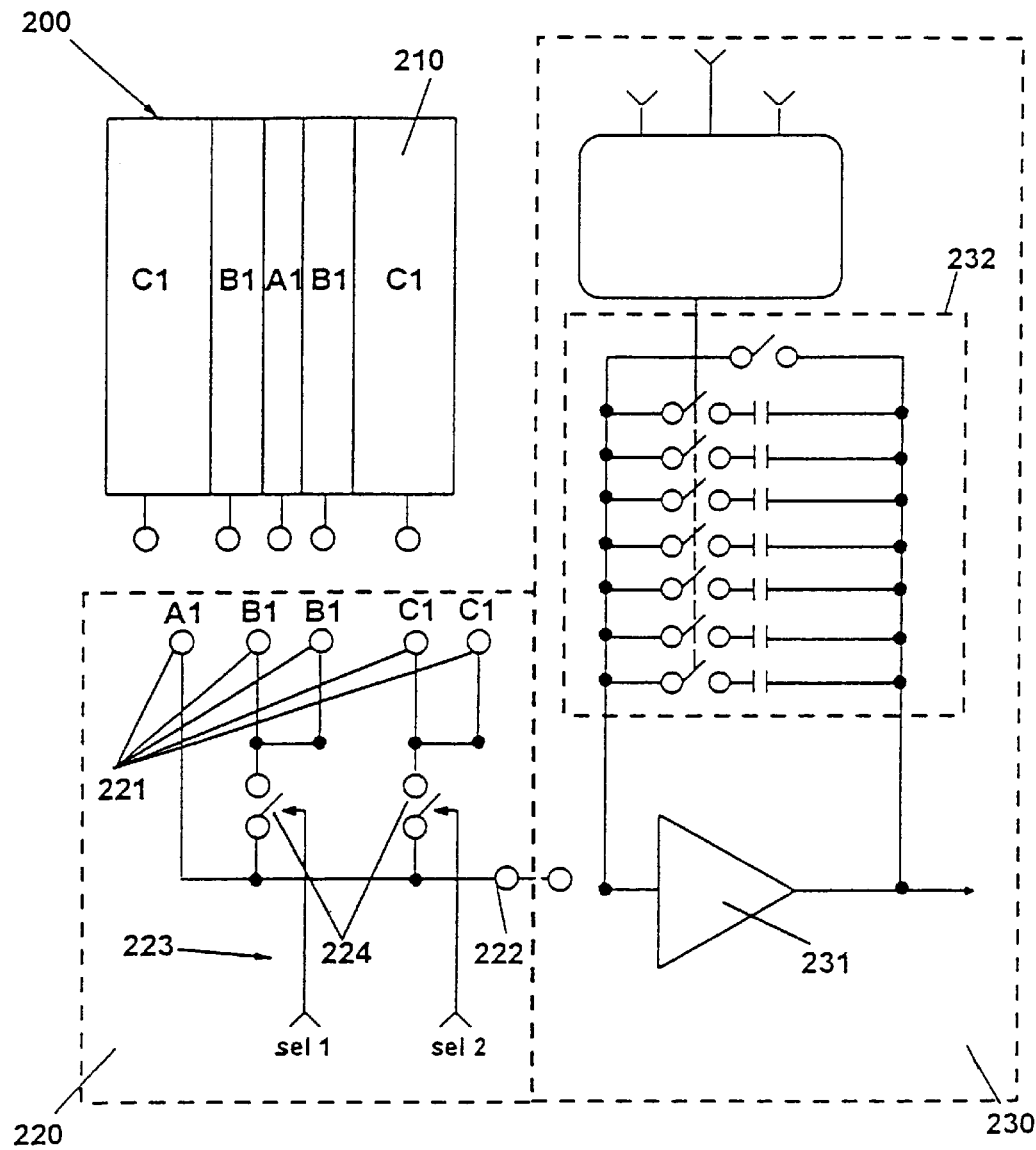
FIG. 2 shows a detector device according to a second embodiment of the invention.

FIG. 2 shows a second embodiment of a detector device 200 according to the present invention.

Compared to the detector device 100 shown in FIG. 1, the detector device 200 has a slightly modified photo semiconductor array 210 and inputs 221 of the read-out means 220 which are adapted appropriately. Moreover, the detector device 100 and 200 correspond to one another. In the following, it is merely referred to the above specified modification, and regarding the components corresponding to each other, it is referred to their description in connection with FIG. 1. In this respect, it must be noted that the reference numerals of elements corresponding to each other only differ by their first number.

In contrast to the photo semiconductor array of the first embodiment, the photo semiconductor array 210 comprises a photo semiconductor device A1 as well as two photo semiconductor devices B1 and C1. The two photo semiconductor devices B1 and the two photo semiconductor devices C1 are each formed identically. Whereas the heights of the two photo semiconductor devices A1, B1 and C1 are equal, the photo semiconductor devices differ by width. In relation to one another, the photo semiconductor devices BE1 and C1 area each arranged symmetrically around the photo semiconductor device A1.

Corresponding to this symmetric arrangement of the photo semiconductor devices, the read-out means 220 is modified with respect to the read-out means 120 shown in FIG. 1.

The read-out means 220 in particular comprises five inputs 221, one of the above specified photo semiconductor devices each being assigned to these inputs.

Moreover, the photo semiconductor device Al is directly connected to the output 222 of the read-out means 220. Therefore, the charge generated in the photo semiconductor device Al is read out during each read-out process. Moreover, one switch 224 each, controlled directly according to FIG. 2 by two selection signals sel1 and sel2, respectively, is associated to the two photo semiconductor devices B1 and C1, respectively.

By closing the switch 224, which is assigned to the two photo semiconductor devices B1, the photo semiconductor devices B1 are connected to the output 222 of the read-out means. Thus, the charges in this configuration which are generated in the photo semiconductor device Al and in the two photo semiconductor devices B1, are read-out by the read-out means 220 and are supplied to the output 222 in form of an electric signal.

If furthermore, switch 224 is closed which is assigned to the two photo semiconductor devices C1, all photo semiconductor devices are connected to the output 222. Consequently, all charges that are generated in the photo semiconductor devices A1, B1, C1 are read-out and supplied to the output 222 of the read-out means 220.

Figure 3:
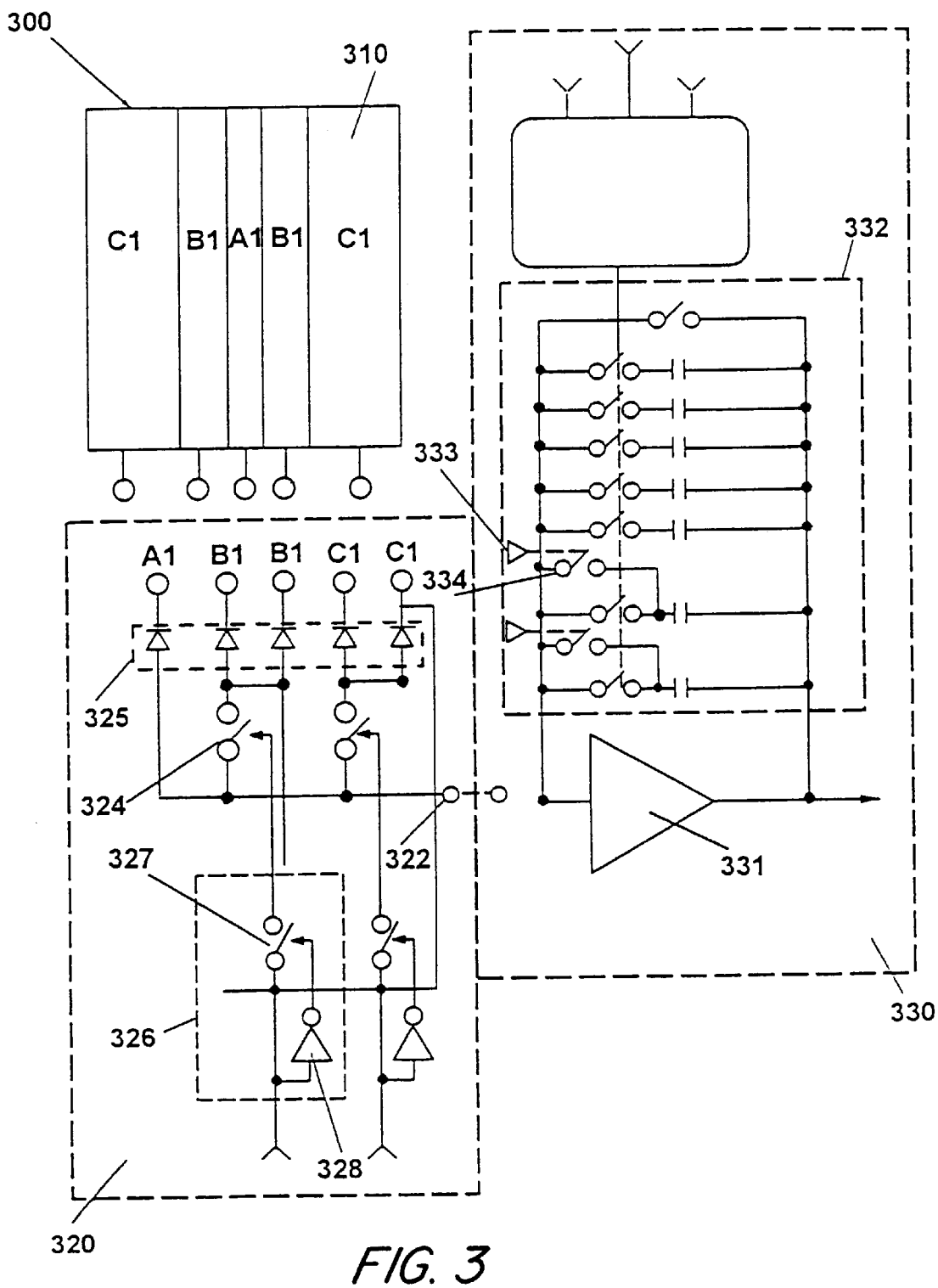
FIG. 3 shows a detector device according to a third embodiment of the invention, FIGS. 4A and B show a detector device according to a fourth embodiment of the invention.

FIG. 3 shows a third embodiment of a detector device 300.

This embodiment differs from the embodiment shown in FIG. 2 in that power limiting means 325 provided in the form of diodes, are additionally provided in its read-out circuit 320, said power limiting means being provided directly downstream the inputs associated to the respective photo semiconductor devices A1, B1 and C1.

These power limiting means 325 ensure that the read-out circuit starts only after a predetermined threshold value to read-out the charges from the respective photo semiconductor devices.

Furthermore a device 326 is provided according to FIG. 3, which puts all photo semiconductor devices to a common predetermined potential which are not coupled to the output 322 of the read-out means 320 because of the position of the switches 324.

According to the embodiment shown in FIG. 3, this device 326 comprises switches 327 and inverters 328. Each switch 327 is associated to one of switches 324. Each switch 327 is provided between the input assigned to this switch 324 and the common potential.

Each switch 327 may be controlled according to FIG. 3 by means of the same selection signal that is used for controlling the switch 324 associated thereto. If the switches 324 and 327, as in FIG. 3, are of the same type, i.e. if they are for instance opened by a high-level signal and closed by a low-level signal, the selection signal for controlling one of the switches 324 or 327 is inverted; in case of the arrangement shown in FIG. 3, the selection signal for instance for controlling the switch 327 is inverted by means of an inverter 328.

This structure leads to the fact that a pair of switches 324 and 327 assigned to each other always comprise switch positions opposite to each other, i.e. if one of the switches 324 and 327 is closed, the other one is opened. Therefore, a photo semiconductor device which is not coupled to the output 322 of the read-out means 320 because of an open switch 324, will be put to the common potential by means of the closed switch 327. This prevents that a photo semiconductor device from which charges are not to be read out, supplies signals to the output 322 of the read-out circuit.

Moreover, external terminals 333 are provided in the variable capacitance 322 according to FIG. 3 with respect to the detector device shown in FIG. 2.

The power limiting means 325, the means 326 as well as the external terminals 333 in this embodiment are obviously preferred embodiments of the detector device which are independent from one another. Therefore, these three preferred embodiments may be used individually or in any combination with one another.

The remaining elements of the embodiment shown in FIG. 3 correspond to the elements shown in FIG. 1 and FIG. 2, respectively. For a detailed description of these element, it may therefore be referred to the respective description in connection with these Figures. In this respect, it must be noted that reference numerals of the respective element only differ from one another by their first number.

Figure 4A:
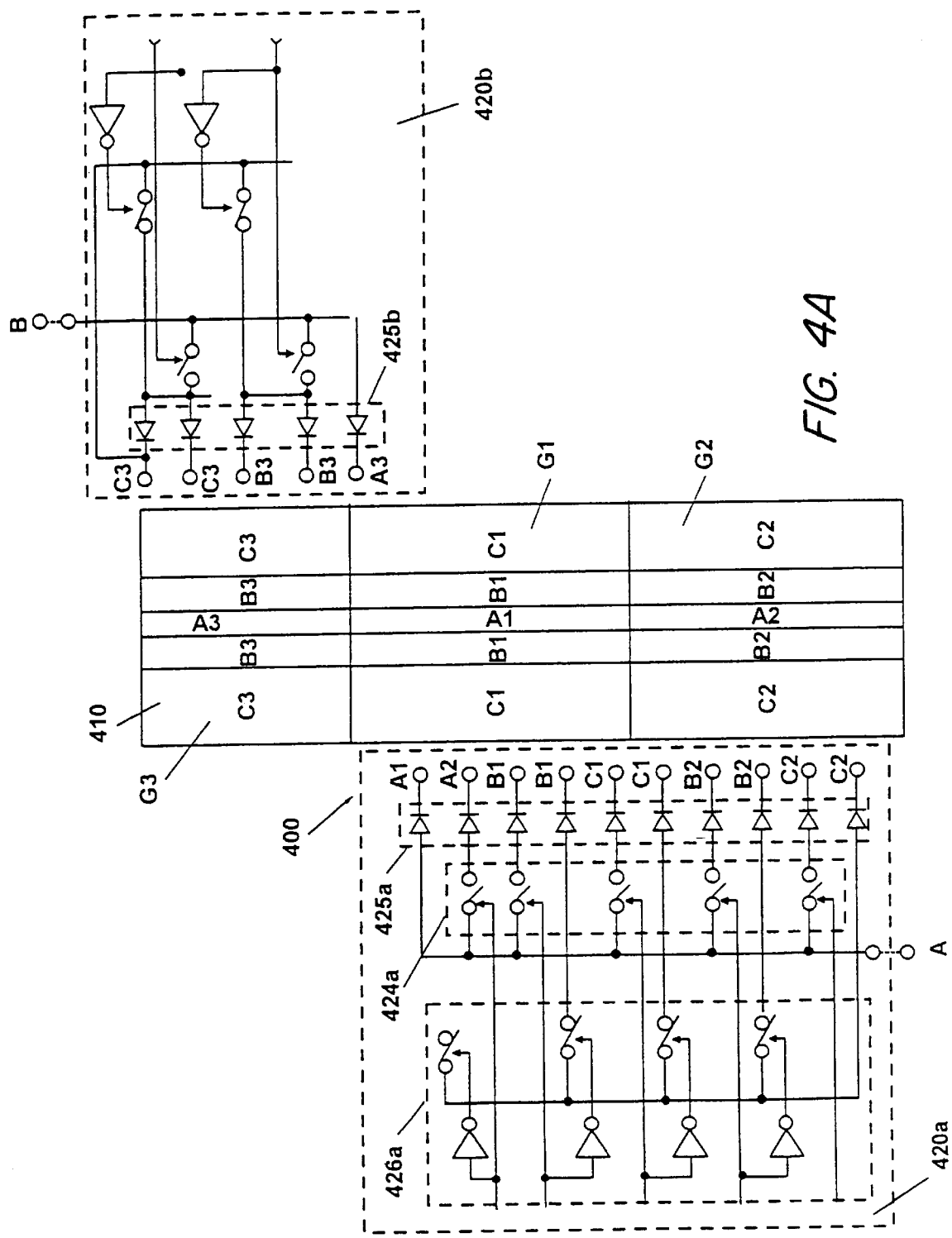
Figure 4B:
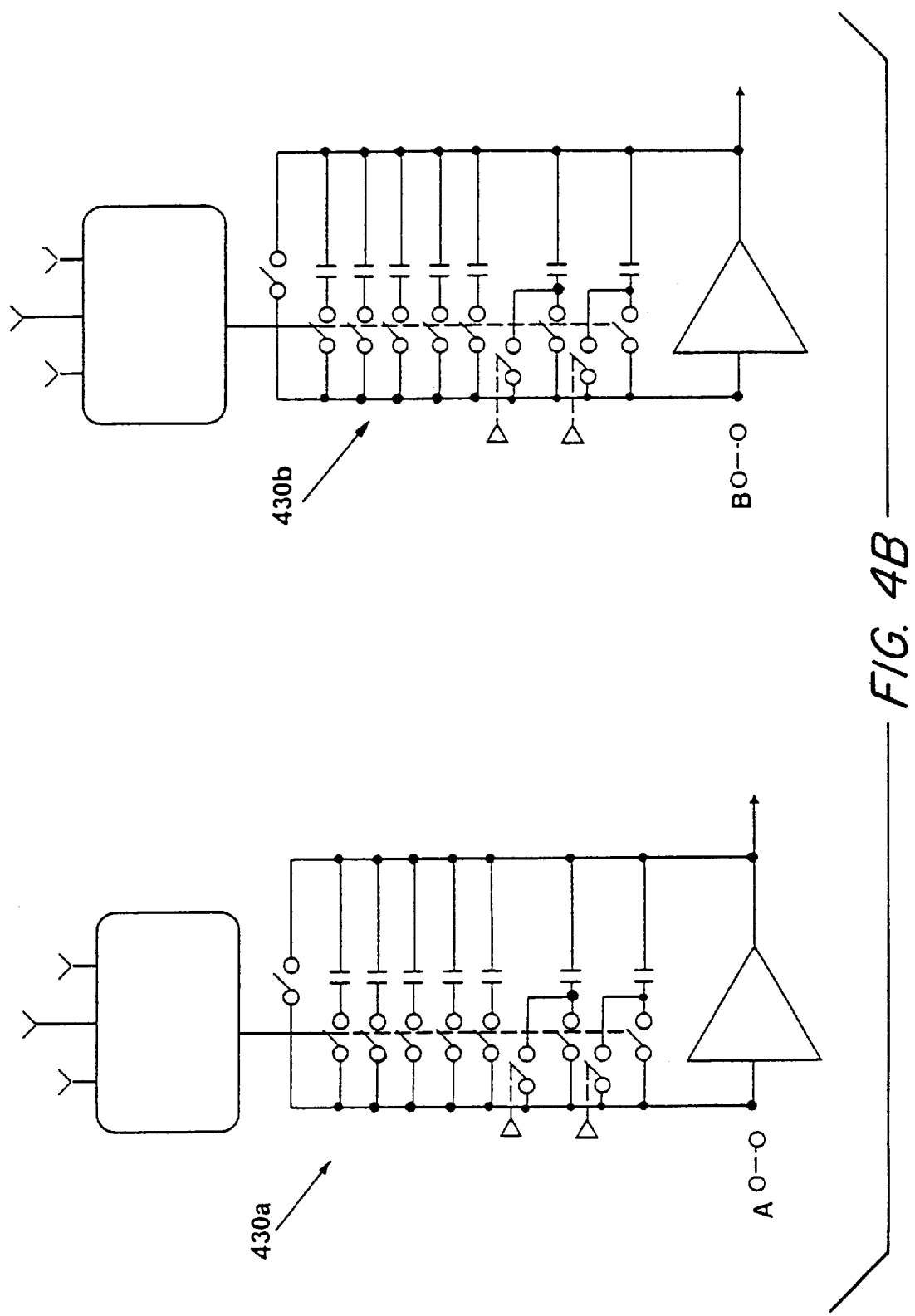

FIG. 4A and 4B show a further embodiment of a detector device 400. This detector device may in particular be used as a universal detector for a plurality of applications in the atomic absorption spectroscopy.

This detector device 400 comprises a photo semiconductor array 410 having fifteen photo semiconductor devices. These photo semiconductor devices are provided in the form of three groups G1, G2 and G3, each having five photo semiconductor devices A1, B1 and C1, A2, B2 and C2, and A3, B3 and C3, respectively.

The individual groups of the photo semiconductor devices are structured analogously to photo semiconductor array shown in FIG. 2. Therefore, one photo semiconductor device A1, A2 and A3, respectively, is provided around which two photo semiconductor devices B1, B2 and B3, respectively, and two further photo semiconductor devices C1, C2, and C3, respectively are symmetrically arranged.

A first read-out means 420a is provided for the first and the second group, and a second read-out means 420b is provided for the third group. Furthermore a first amplification means 430a and a second amplification means 430b are provided, respectively.

The read-out means 420a corresponds to the read-out means 320 of FIG. 3, wherein corresponding to the additional photo semiconductor devices A2, B2 and C2, additional elements 424a, 425a and 426a are provided.

The read-out means 420b corresponds to the read-out means 320 in FIG. 3.

The amplification means 430a and 430b, besides the external terminals described in connection with FIG. 3, are also identical with the amplification means 130. To describe these circuits, it may be referred to the relevant description of FIG. 1 and FIG. 3.

The arrangement of photo semiconductor devices in the detector array 410 shown in FIG. 4A, enables a universal use of the detector device in a plurality of different applications in the atomic absorption spectroscopy.

By means of read-out of groups G1 and G3, two beams which have passed through different optical paths may for instance be simultaneously measured by the detector device and may be evaluated subsequently.

When using a gap monochromator, the height of the gap formed onto the photo semiconductor array can be adjusted by selective read-out of groups G1, G2 or G1 and G2. Thus, it is possible, for instance, to adapt by means of the read-out means the gap height to the atomic absorption method used.

Furthermore, the width of the photo semiconductor array used as a proof can be adjusted in a simple manner for each group by selecting the respective photo semiconductor devices, as already explained in connection with FIG. 2.

What is claimed is:

1. A photoelectric detector device to be used in atomic absorption spectroscopy, characterized by:

a photo semiconductor array having a plurality of photo semiconductor devices (A, B, C; A1, B1, C1; A2, B2, C2, A3, B3, C3), and read-out means (120; 220; 320, 420a, 420b) for reading out charges generated by impingement of radiation in the photo semiconductor devices, of any continuous portion in the photo semiconductor array, and for generating electric signals corresponding to the read-out charges, said readout means including plurality of inputs (121, 221) each coupled to a photo semiconductor device of the photo semiconductor array.

an output (122, 222) for a signal from the input and which output corresponds to read-out charges from photo conductor devices, switching means (123, 223) interposed between the inputs and the output and connecting selected inputs to the output so as to deliver a signal representative of the combination of the selected inputs to the output, the switching means having at least one switch downstream from and associated with a plurality of the inputs to couple the associated inputs with the output of the read-out means.

2. A detector device as claimed in claim 1, in which each switch (124; 224) of the switching means (123; 223) is electrically operative.

3. A detector device as claimed in claim 1 in which each switch (324) has additionally associated thereto a means (326) which couples all photo semiconductor devices which are not coupled to the output of the read-out means (320) to a predetermined potential.

4. A detector device as claimed in claim 3, in which each means (326) associated to a switch (324) comprises a further switch (327) which is provided between the input associated to the switch (324) and the predetermined potential in a manner that it couples the input to the predetermined potential when it is not coupled to the output of the readout means.

5. A detector device as claimed in claim 4, in which each switch (324) and each further switch (327) associated therewith are operative by an electric signal which is directly supplied to the switch (324) and which is supplied to the switch (327) via an inverter (328).

6. A detector device as claimed in claim 2 in which a decoder means (125) is provided which operates the switch or the switches (124) in response to digital selection signals (SEL1, SEL2).

7. A detector device as claimed in claim 1, in which the photo semiconductor devices (A, B, C; A1, B1, C1; A2, B2, C2, A3, B3, C3) are provided in form of photo diodes.

8. A photoelectric detector device (100; 200; 300; 400) to be used in the atomic absorption spectroscopy, characterized by a photo semiconductor array (110; 210, 310; 410) having a plurality of photo semiconductor devices (A, B, C; A1, B1, C1; A2, B2, C2, A3, B3, C3), and a read-out means (120; 220; 320, 420a, 420b) for reading out the charges generated by impingement of radiation in the photo semiconductor devices, of any continuous portion of the photo semiconductor array, and for generating electric signals corresponding to the read-out charges; said readout means further including:

a plurality of inputs (121; 221) each coupled to a photo semiconductor device in the photo semiconductor array, an output (122, 222) for a signal from the inputs and which output corresponds to the read-out charges, switching means (123; 223) interposed between the inputs and the output and connecting selected ones of the inputs to each other so as to deliver a single signal representative of the combination of the selected inputs to the output; and power limiting means (325; 425a, 425b) provided directly downstream of each input of the read-out means.

9. A detector device as claimed in claim 8 in which the power limiting means is provided in the form of a diode.

10. Photoelectric detector device (100; 200; 300; 400) to be used in the atomic absorption spectroscopy, characterized by a photo semiconductor array (110; 210, 310; 410) having a plurality of photo semiconductor devices (A, B, C; A1, B1, C1; A1, B1, C1, A2, B2, C2, A3, B3, C3), and a read-out means (120; 220; 320, 420a, 420b) for jointly reading out the charges generated by impingement of radiation in the photo semiconductor devices of any continuous portion of the photo semiconductor array, and for generating electric signals corresponding to the read-out charges;

amplification means (130; 320; 330, 430a, 430b) for amplifying the electric output signals of the read-out means, said amplification means comprising:

an operational amplifier (131; 231; 331), and a variable capacitance (132; 232; 332) connected in parallel with the amplifier.

11. A detector device as claimed in claim 10, in which the variable capacitance (132; 232; 332) comprises a plurality of parallel connected rows each composed of one capacitor (133) and one switch (134), and the capacitance is variable by operating at least one of the switches (134).

12. A detector device as claimed in claim 11, in which a switch (136) is provided in parallel to the rows each composed of one capacitor and one switch.

13. A detector device as claimed in claim 11, in which a decoder means (135) is provided which operates the switches (134) in response to digital selection signals (SEL1, SEL2, SEL3).

* * * * *